US010073057B2

(12) United States Patent
Melo Hurtado et al.

(10) Patent No.: US 10,073,057 B2
(45) Date of Patent: Sep. 11, 2018

(54) MICRO MAGNETIC TRAP AND PROCESS FOR EVALUATING FORCES WITH PICO NEWTON RESOLUTION

(71) Applicant: Universidad de Santiago de Chile, Santiago (CL)

(72) Inventors: Francisco Esteban Melo Hurtado, Santiago (CL); Romina Waleska Muñoz Buzeta, Santiago (CL); Felipe Andrés Aguilar Sandoval, Santiago (CL)

(73) Assignee: Universidad de Santiago de Chile (CL)

( * ) Notice: Subject to any disclaimer, the term of this patent is extended or adjusted under 35 U.S.C. 154(b) by 0 days.

(21) Appl. No.: 15/182,457

(22) Filed: Jun. 14, 2016

(65) Prior Publication Data

US 2017/0356932 A1    Dec. 14, 2017

(51) Int. Cl.
| | | |
|---|---|---|
| *G01Q 60/54* | (2010.01) | |
| *G01N 27/72* | (2006.01) | |
| *G01Q 60/42* | (2010.01) | |

(52) U.S. Cl.
CPC ............. *G01N 27/72* (2013.01); *G01Q 60/42* (2013.01); *G01Q 60/54* (2013.01)

(58) Field of Classification Search
None
See application file for complete search history.

(56) References Cited

U.S. PATENT DOCUMENTS

| 5,807,758 A * | 9/1998 | Lee ................. B82Y 35/00 422/82.01 |
| 5,983,712 A * | 11/1999 | Lindsay ............ B82Y 35/00 73/105 |
| 9,645,144 B2 * | 5/2017 | Torun .............. G01N 33/54366 |
| 2003/0222649 A1 * | 12/2003 | Fainchtein ......... G01R 33/022 324/321 |
| 2004/0113621 A1 * | 6/2004 | Naughton ........... B82Y 15/00 324/321 |
| 2008/0134771 A1 * | 6/2008 | Schimmel ........... B82Y 35/00 73/104 |
| 2010/0219819 A1 * | 9/2010 | Kimura ............. B82Y 35/00 324/244 |

(Continued)

OTHER PUBLICATIONS

Hartbaum et al. "Magnetic bead nanoactuator", Microelectronic Engineering 2012.*

(Continued)

*Primary Examiner* — Michael Logie
(74) *Attorney, Agent, or Firm* — Tolpin & Partners PC; Thomas W. Tolpin

(57) ABSTRACT

Micro magnetic trap comprising a holder and a sample cell on said holder (5); means for providing a controllable homogeneous magnetic field (3) surrounding the sample cell; a modified micro-cantilever comprising a cantilever (1) having dimensions in the micron range and at least three paramagnetic microbeads with a diameter from 1 to 3 microns (2) attached to a bendable tip of the micro-cantilever such that they form a triangular arrangement; means for measuring the deflection of the micro-cantilever when the latter is in use (4). The trap does not require a specific surface functionalization in order to ensure an appropriate and selective linkage to a particular molecule.

5 Claims, 4 Drawing Sheets

(56) References Cited

U.S. PATENT DOCUMENTS

| | | | |
|---|---|---|---|
| 2011/0294185 A1* | 12/2011 | Sooryakumar | G01N 33/54326 |
| | | | 435/173.9 |
| 2012/0307605 A1* | 12/2012 | Zhang | G11B 5/455 |
| | | | 369/13.32 |
| 2016/0266107 A1* | 9/2016 | Torun | G01Q 10/04 |

OTHER PUBLICATIONS

Weizmann et al., "Magneto-Mechanical Detection of Nucleic Acids and Telomerase activity in Cancer cells", JACS Articles Jan. 8, 2004.*

Baselt et al. "Biosensor based on force microscope technology", J. Vac. Sci. Technol. B, 1996.*

Baselt et al. "A high-sensitivity micromachined biosensor", IEEE, 1997.*

Florin et al. "Atomic force microscope with magnetic force modulation", Rev. Sci. Instrum. Mar. 1994.*

Cowburn et al., "High sensitivity measurement of magnetic fields using microcantilevers", Appl. Phys. Lett. 71, Oct. 13, 1997.*

Pulling on super paramagnetic beads with micro cantilevers: single molecule mechanical assay application, by Romina Muñoz et al, Phys. Biol. 12 (2015) 046011, IOPSCIENCE Organization.

* cited by examiner

MICRO MAGNETIC TRAP AND PROCESS FOR EVALUATING FORCES WITH PICO NEWTON RESOLUTION

BACKGROUND OF THE INVENTION

Field of the Invention

The present invention relates to the field of micro magnetic mechanical systems of micro-cantilevers type, for force measurements and manipulation of small objects such as micro sized beads and macromolecules DNA Description of the Related Art During diverse molecular processes forces are generated inside cells such as transcription or replication of DNA, protein unfolding, translocation of proteins across membranes, and cell locomotion. At present, due to their versatility, atomic force microscopy, and optical and magnetic tweezers are the most commonly used techniques to measure force at the single molecule level. Optical trapping allows for the application of forces and the manipulation of biomolecules such as DNAs, and the detection of folding and unfolding events of proteins at a single molecule level. In addition to forces, magnetic tweezers apply torques on micro-magnetic beads linked to single molecules through the displacement and rotation of the external magnets. An advantage of this methodology is that it generates very stable force fields that can be simultaneously applied to many individual molecules within the field of view of the microscope. Of the aforementioned techniques, a disadvantage of magnetic tweezers is that they have the lowest spatial resolution (5-10 nm), but they are suitable for use with very low forces ($\approx 0.1$ pN) and do not cause radiation heating or photo damage to the sample. Conversely, micro cantilevers have important advantages with respect to magnetic and optical tweezers since they can be manufactured in a broad range of sensing forces and a variety of systems are available to detect their deflections, which provides high accuracy force assessment over a wide dynamic range. However, micro cantilevers have two important disadvantages for the mechanical assessment of single molecules; firstly, the cantilever tip requires a specific surface functionalization in order to ensure an appropriate and selective linkage to a particular molecule, and secondly, following contact with the tip-molecules, several trials and elaborated procedures may be required to ensure that only one single molecule has been linked to the cantilever. In addition, once a molecule has been tested, testing another molecule from the sample (with the same cantilever) requires the breaking of the link in order to create a new link, which increases the uncertainty of the operation of subsequent links. This is a serious limitation when a high number of individual molecules are tested and statistical analysis is required, or when the same molecule has to be tested in a non-destructive manner.

SUMMARY OF THE INVENTION

The micro magnetic trap of the invention comprises a holder and a sample cell on said holder; means for providing a controllable homogeneous magnetic field surrounding the sample cell; a micro-cantilever in the micron range and at least three paramagnetic microbeads (diameter of 1 to 3 microns) attached to a bendable tip of the micro-cantilever such that they form a triangular arrangement; and means for measuring the deflection of the micro-cantilever when the latter is in use. The measuring means are preferably an interferometric system and positioning stage for the cantilever. The magnetic means can be a magnetic coil and associated electric circuit or alternatively permanent magnets and mechanical means for approaching or moving away the magnets from the center of the probe cell. The associated method for evaluating forces generated at the micro scale comprises the steps of placing a tethered paramagnetic micro-bead in front of the bendable end of the micro-cantilever; turning the magnetic means on and measuring the force exerted on the micro-cantilever by measuring its deflection when the tethered micro-bead is trapped. Thus, the present invention provides a device and method that overcome the disadvantages disclosed in the prior art.

BRIEF DESCRIPTION OF THE DRAWINGS

To complete the description and provide for better understanding of the invention, a set of drawings is provided. Said drawings illustrate a preferred embodiment of the invention, which should not be interpreted as restricting the scope of the invention, but just as an example of how the invention can be carried out.

DESCRIPTION OF THE PREFERRED EMBODIMENTS

Figure 1:
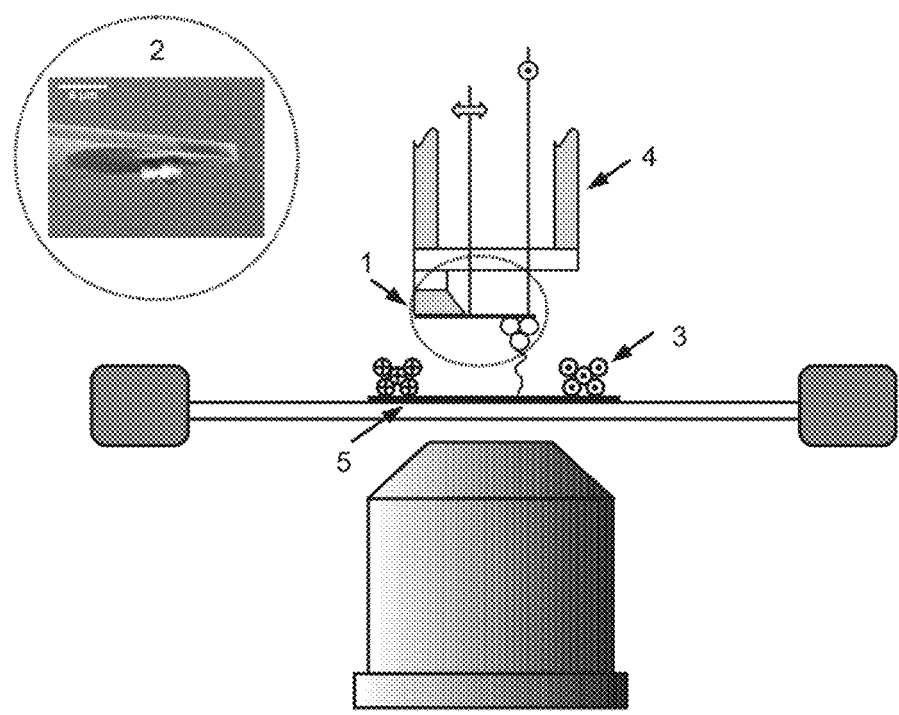
FIG. 1 is a scheme of the invention when using coils as the magnetic means.
Figure 2:
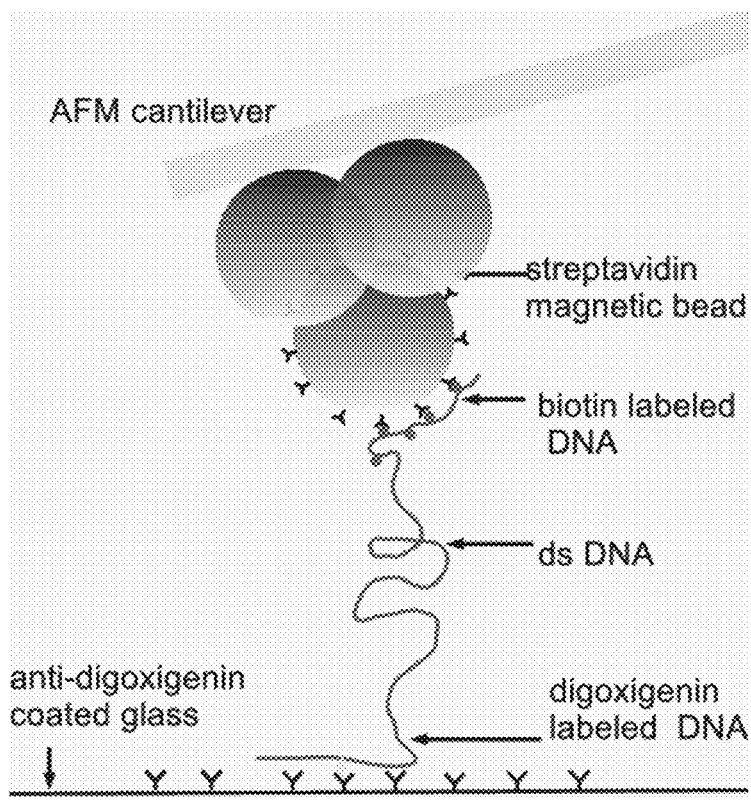
FIG. 2 shows the working principle of the micro cantilever used in the invention.

A schematic representation of the present invention is shown in FIG. 1. The invention comprises a magnetic trap that consists of three super paramagnetic micro beads (2) with diameters between 1 and 3 microns with centers forming the vertex of an equilateral triangle, the three micro beads attached to the tip of a micro cantilever (2) by means of, for example, an epoxy layer. In the presence of a constant external magnetic field generated by coils (3) or other means, beads are magnetized and cause strong field gradients in neighboring regions. Therefore, if a fourth super paramagnetic bead, polarized by the external field, approaches the trap from a sufficiently short distance, it experiences attractive dipolar forces (1).

A coil or several magnets (3) positioned concentrically to a sample cell (5) (preferably, but not necessarily a fluid sample) generate a small homogeneous magnetic field in the area of interest. The latter can be increased or decreased by varying the current within the coil. In the case of magnets, the field can be varied by mechanical means, as it will be explained. Changes in the magnetic field allow for either trapping or releasing a tethered bead without damaging any molecules, as the field changes smoothly. An electric circuit manages the variation of the current.

A variety of well-known methods can be used to determine the force exerted on the cantilever. To reduce errors and increase sensitivity, an interferometric system (4) is preferred. A quadrature phase system for detecting absolute deflection and improving sensitivity and low force noise is used. Two parallel beams at approximately 700 µm apart impinge simultaneously on the bendable part of the cantilever and its rigid base (1). The beams are of perpendicular relative polarization and are obtained from a He—Ne single beam by means of a calcite beam displacer. Thus, the cantilever deflection induces a phase difference, φ, in the reflected beams, which is detected as a contrast of intensities at two pairs of photodiodes. The contrast in one pair is cos(φ), and in the other pair it is sin(φ) due to the presence of the λ/4 plate. Thus, in a polar representation, the contrast describes a circle of constant radius, which ensures constant sensitivity over the whole domain φ and of the cantilever deflection. Losses due to the reflection of laser beams are minimized by using an anti-reflex window that also serve as the upper lid of the fluid cell. In addition, a spacer of 1 mm thickness allows the cantilever to be fixed parallel to the lower face of this window.

In order to provide an estimate of the force applied to a bead by the trap, we consider that the external field ($\vec{B}_0$) is homogenous within close proximity to the trap and is responsible for inducing a magnetization on each bead within the trap. To mathematically describe our magnetic system, we approximate each bead to a magnetic dipole whose moment is proportional to the external field. In addition, we neglect any magnetic influence of the cantilever. Thus, $\vec{m} = V_b \chi_b \vec{B}_0 / \mu_0$ where $\chi_b$ is the magnetic susceptibility and $V_b$ is the volume of the super paramagnetic bead. The force acting on the active bead is then, $$\vec{F} = \nabla(\vec{m}_b \cdot \vec{B}_T). \quad (1)$$

Where $\vec{B}_T$ is the total magnetic field, which we have approximated as the linear superposition of the external field plus the field produced by the induced dipole moments on the trap $\vec{B}_t$. Since the external field is nearly homogeneous and directed along the vertical $\hat{z}$, equation (1) becomes, $$\vec{F} = \frac{V_b \chi_b B_0}{\mu_0} \nabla(\hat{z} \cdot \vec{B}_t), \quad (2)$$

which provides an estimate of the vertical magnetic force exerted by the trap on the active bead located at the point of coordinates (x, y, z)

$$F_z = \frac{V_b \chi_b B_0}{\mu_0} \frac{\partial}{\partial z}(B_{t,z}(x, y, z)) \quad (3)$$

The magnetic field provided by the trap is approximated to that of three magnetic induced dipoles ($m_i$, with $i=1,2,3$) arranged in an equilateral triangle. Thus, the trap field reads $$\vec{B}_t = \frac{\mu_0}{4\pi} \left[ \sum_{i=1}^{3} \left( \frac{3\vec{r}_i(\vec{m}_i \cdot \vec{r}_i)}{r_i^5} - \frac{\vec{m}_i}{r_i^3} \right) \right],$$

where $\vec{r}_i = \vec{r} - \vec{a}_i$, while $\vec{r}$ describes the point in space and $\vec{a}_i$ indicates the vertex of the equilateral triangle with a base equal to the beads diameter, defined by the center of the beads with radius R and $(\vec{a}_i) = a = 2R/\sqrt{3}$. Since the external field is along $\hat{z}$ and the micro beads are assumed to have equal properties, the induced dipole moments can be written as $\vec{m}_i = (V_b \chi_b B_0 / \mu_0)\hat{z}$. After replacing $m_i$ in equation (4) and then in equation (3), the vertical force on the active beads located at a distance z, along the axis of symmetry reads, $$F_z(0, 0, z) = \frac{3V_b^2 \chi_b^2 B_0^2}{4\pi \mu_0} \frac{z}{(z^2 + a^2)^{5/2}} \frac{9a^2 - 6z^2}{z^2 + a^2} \quad (5)$$

The closest approach distance for the active bead in the trap is $z_{min} = \sqrt{2/32}$ R. The magnetic force at contact then becomes, $$F_z(0, 0, z_{min}) = \frac{-\sqrt{6} V_b^2 \chi_b^2 B_0^2}{64 \pi \mu_0 R^4} \quad (6)$$

Using, for example, Dynabeads with R=1.4 μm, the maximum force applied to the trap can easily exceed 100 pN through an increase in the external field. The invention has thus a wide range of uses, such as DNA assessment.

The process of trapping and releasing paramagnetic micro-beads by means of switching on and off a magnetic field in a coil can induce significant heat dissipation, which can negatively affect force measurements through microcantilever deflection. Thus, the use of coils can introduce some thermal drift, which must be avoided when a high level of sensitivity in the force assessment is desired (below a few pN).

Figure 3:
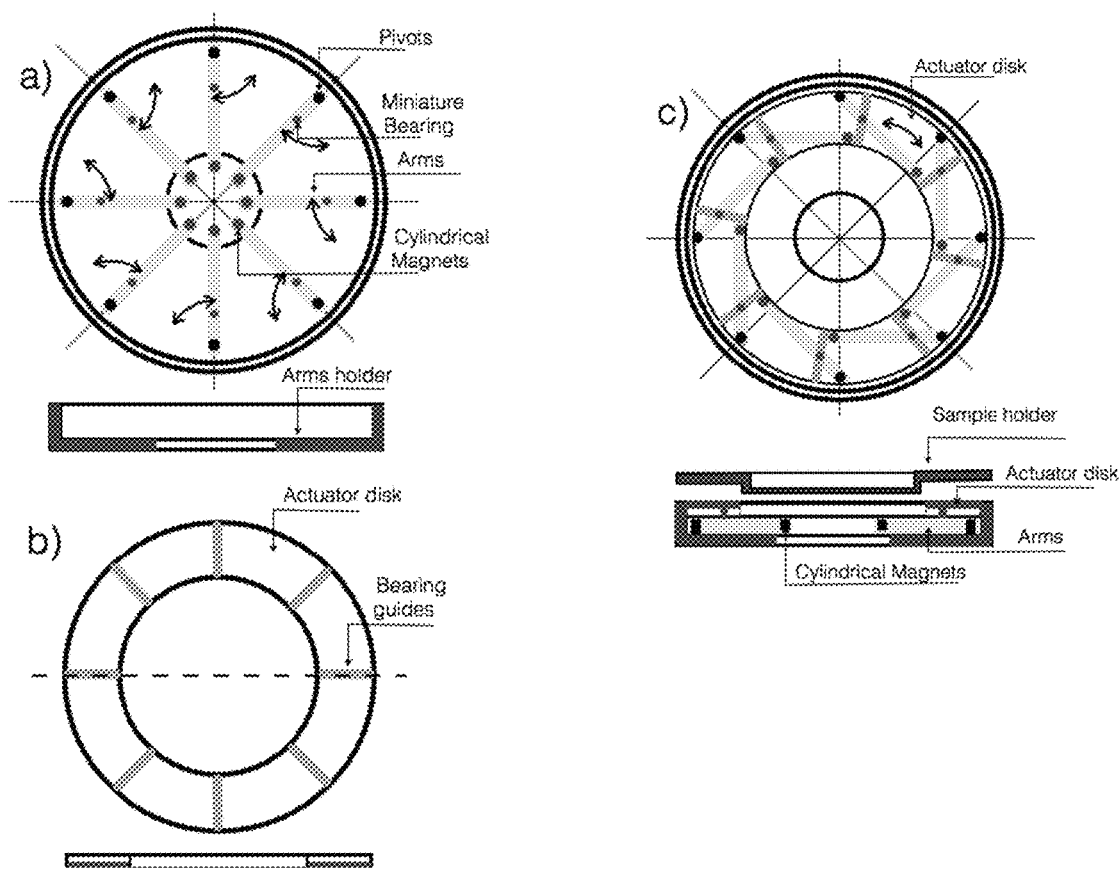
FIG. 3 shows a mechanical device for use when the magnetic means are permanent magnets.

One manner of avoiding heating associated with the magnetic field is by using a ring shaped permanent magnet. However, with such configuration, setting the magnetic field off at the region of interest demands removing the magnet, which is a cumbersome process due to the limited space below the cell and the presence of the microscope lenses. In order to overcome this difficulty, a mechanical device able to radially approach and move away several magnets has been designed. Functioning of the device is schematized in the panels of FIG. 3. Small cylindrical magnets are located at each end of n arms (8 in this case, FIG. 3a). Poles of magnets are aligned along the principal axis of the cylinders and arranged in such a way that all contribute with the same magnetic field at the center of the cell. In addition, the angular configuration preserves symmetry providing a zone of constant magnetic field near the center. Arms are allowed pivoting at the other extreme (FIG. 3a). Starting from the situation presented in the FIG. 3a, when all arms pivot simultaneously the same angle in the same direction (with the help of the device depicted on FIG. 3b), all magnets move away the same distance from the center (FIG. 3c), which significantly reduces the magnetic field in the region of interest. Thus, the magnetic force is reduced gradually (switching off process) without inducing severe gradients of magnetic field, reducing damage to the molecules under study. Simultaneous motion of arms is achieved by gradually rotating of a second concentric disk (FIG. 3b), placed on top of the arms array (FIG. 3c). During rotation, miniature bearings depicted in FIG. 3a, fit on the grooves of the disk and act on each arm forcing simultaneous rotation of all arms.

EXAMPLES

Streptavidin coated Dynabeads (2.8 μm) are diluted in milliQ water at concentrations of 50 ng/μL. A 10 μL volume of the resulting solution is deposited onto a glass slide and left exposed to the atmosphere to dry. To eliminate salt traces, micro beads are further rinsed with distilled water, however as a result of this process some micro beads will be lost. Under an inverted optical microscope (Nikon Eclipse), a tip-less micro cantilever with nominal force constant 0.03 N/m (Arrow-TL1 from Nano World), previously attached to the arm of a three-axis water hydraulic micromanipulator with a minimum graduation of 0.2 μm (MHW-3, from Narishige), facilitates some micro beads to group into triangular clusters of three particles. Each micro bead is separated from one another by a sufficient distance, which allows for beads manipulation without interference (about 100 μm). Slow curing epoxy adhesive provides strong attachment of clusters to the cantilevers and allows enough time for manual positioning. To avoid an excess of adhesive, a thin layer of epoxy is prepared onto the glass slide a few millimeters distance from the cluster area. The sensitive end of the tip-less cantilever is brought close to the adhesive until contact is made and some adhesive is transferred to the surface by capillarity action. The cantilever is then gently pushed against the selected cluster. Prior to use the cantilever-trap is left to dry at room temperature for several hours.

Figure 4:
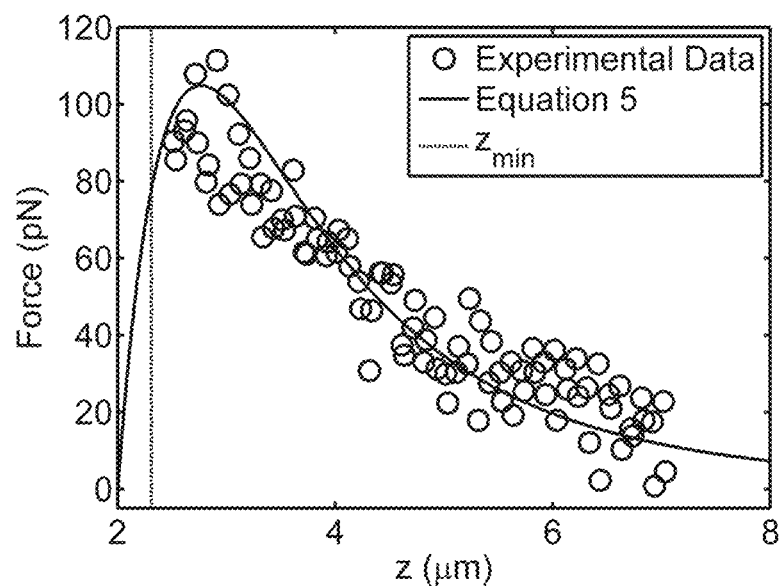
FIG. 4 shows measurements of the force exerted by the trap on a microsphere as a function of its distance to the trap.

A coil positioned concentrically to the fluid cell (FIG. 1), generates a small homogeneous magnetic field in the area of interest. This can be increased or decreased by varying the current within the coil, allowing for either the trapping or releasing of a tethered bead. An electric circuit manages the variation of the current. The magnetic field is measured with a magnetic field sensor (sensitivity $9 \times 10^{-4}$ G). To characterize the magnetic trap, the force exerted on a microsphere fixed onto the bottom of a glass cell, as a function of the vertical distance, was calculated. In order to simplify the process, in the absence of magnetic field, the magnetic trap was located just above the bead at a distance of about 6 μm. The magnetic interaction was measured through the detection of cantilever deflection and carried out in a fluid environment. The measurement is carried out by generating cycles of current, which in turn produced cycles of a magnetic field (of about 200 G amplitude for 0.2 s and 0 G for 0.8 s), simultaneously the cantilever approaches the bead at a constant velocity of 100 nm s−1. The magnetic force was then modulated at the same frequency, which allows for the minimization of thermal drift on the cantilever detection caused by the heating up of the coil. Thus, the magnetic force was obtained through the envelope of the cantilever deflection multiplied by the cantilever stiffness. In FIG. 4 the resulting force is contrasted against the predictions obtained from equation (5). The solid line represents the best fit using the magnetic field as a fitting parameter. Equation (5) provides a satisfactory explanation for the magnetic force.

In order to trap a tethered bead, the trap is directly positioned above the selected bead at a distance of less than 1 μm in the absence of a magnetic field.

Figure 5:
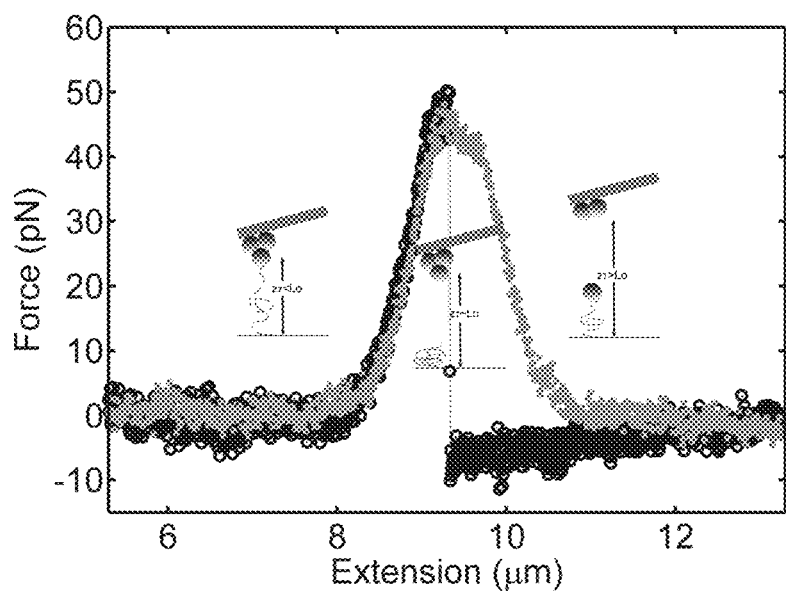
FIG. 5 shows measurements of the force exerted by the modified cantilever on a DNA molecule attached to a micro bead.

The magnetic field is then switched on, which induces the bead to lodge into the cavity of the trap. It is found that a field of 80 G is both sufficient and avoids over heating. Force curves are then obtained through the vertical displacement of the sample, which is achieved by means of the high performance piezoelectric stage. FIG. 5 presents the force exerted by the cantilever on a DNA tethered molecule as function of the DNA extension, this was determined by measuring the distance from the bottom cell to the location of the tethered bead in the magnetic trap. The force rapidly increases as the DNA molecule stretches and approaches an extension close to its contour length.

However, at relatively low B0 (≈80 G) and sufficiently high DNA stress (in this case approximately 50 pN), the tethered bead can detach from the magnetic click. After detachment, the DNA molecule retracts (see rightmost inset of FIG. 5).

Two polarized parallel lasers beams impinge upon the sensitive cantilever part and the cantilever body. After reflection, the phase difference is detected by the quadrature phase interferometer, which provides the cantilever deflection. As an optional alternative, it is possible to use a pair of ring magnets in order to avoid the overheating of the coil from long periods of use, this option restricts the coil use for only disconnecting the trapped bead. The magnetic field is then switched on, which induces the bead to lodge into the cavity of the trap.

As it is used herein, the term "comprises" and derivations thereof (such as "comprising", etc.) should not be understood in an excluding sense, that is, these terms should not be interpreted as excluding the possibility that what is described and defined may include further elements, steps, etc.

On the other hand, the invention is obviously not limited to the specific embodiment(s) described herein, but also encompasses any variations that may be considered by any person skilled in the art (for example, as regards the choice of materials, dimensions, components, configuration, etc.) to be within the general scope of the invention as defined in the claims.

What is claimed is:

1. A micro magnetic trap, to allow either trapping or releasing a paramagnetic micro-bead from a fluid with tethered paramagnetic micro-beads, comprising:
    a holder and a sample cell on said holder (5) comprising a center and a radial axis extending therefrom;
    means for providing a controllable homogeneous magnetic field (3) surrounding the sample cell;
    a micro-cantilever (1) having dimensions in the micron range and at least an arrangement of three paramagnetic microbeads (2) attached to a bendable tip of the micro-cantilever; and
    an interferometric system for measuring the deflection of the micro-cantilever when the latter is in use (4);
    wherein the means for providing the controllable homogeneous magnetic field are a plurality of permanent magnets and mechanical means for approaching or moving away the permanent magnets from the center of the sample cell, and
    wherein the mechanical means comprise arms with ends and a concentric disk with groove placed on top the arms;
    wherein the permanent magnets are located at one end of the arms, and another end of the arms comprise a pivoting end, and
    the concentric disk comprises a plurality of miniature bearings that fit on the grooves of the disk forcing the simultaneous rotation of the arms, allowing the coordinated movement of permanent magnets in the radial axis.

2. The micro magnetic trap according to claim 1, wherein the three paramagnetic microbeads are in a triangular arrangement.

3. The micro magnetic trap according to claim 1, wherein the paramagnetic microbeads have dimensions of 1 to 3 microns.

4. A method for evaluating forces generated at the micro scale by means of the micro magnetic trap according to any of the previous claims comprising the steps of:
    placing the fluid with the tethered paramagnetic microbeads to be measured into the sample cell;
    placing a tethered paramagnetic micro-bead of the sample cell in front of the bendable end of the micro-cantilever;

generating the controllable homogenous magnetic field, approaching gradually to the center of the sample cell with the permanent magnets; and measuring the force exerted on the micro-cantilever by measuring its deflection when the tethered micro-bead is trapped.

5. The method according to claim 4, wherein the controllable homogeneous magnetic field ranges from 10 G to 200 G.

* * * * *

UNITED STATES PATENT AND TRADEMARK OFFICE
CERTIFICATE OF CORRECTION

PATENT NO. : 10,073,057 B2  
APPLICATION NO. : 15/182457  
DATED : September 11, 2018  
INVENTOR(S) : Francisco Esteban Melo Hurtado et al.

Page 1 of 1

It is certified that error appears in the above-identified patent and that said Letters Patent is hereby corrected as shown below:

On the Title Page

Item (72), Inventors:  
Insert at the end thereof the following inventor --Christian Wilson, Santiago (CL)--

Signed and Sealed this
Twenty-eighth Day of May, 2019

Andrei Iancu
*Director of the United States Patent and Trademark Office*